United States Patent [19]

Hitchcock

[11] 4,220,552

[45] Sep. 2, 1980

[54] METHOD OF PRODUCING DELAYED RELEASE OF SODIUM FLUORIDE

[75] Inventor: Charles J. Hitchcock, Cambridge, Mass.

[73] Assignee: The United States of America as represented by the Department of Health, Education & Welfare, Washington, D.C.

[21] Appl. No.: 912,946

[22] Filed: Jun. 5, 1978

[51] Int. Cl.$^2$ .......................... B01J 13/02; B44D 1/02
[52] U.S. Cl. ...................................... 252/316; 424/52; 427/3
[58] Field of Search ..................... 106/197 R; 252/316; 424/151, 52; 427/3

[56] References Cited

U.S. PATENT DOCUMENTS

| | | | |
|---|---|---|---|
| 1,448,091 | 3/1923 | Seel | 536/89 |
| 2,840,485 | 6/1945 | Greminger | 106/197 R |
| 3,312,594 | 4/1967 | Cyr | 424/151 |
| 3,345,265 | 10/1967 | Grodberg | 424/52 |
| 3,415,758 | 12/1968 | Powell | 424/32 |
| 3,951,851 | 4/1976 | Kitajima | 252/316 |

FOREIGN PATENT DOCUMENTS

| | | | |
|---|---|---|---|
| 1001205 | 8/1965 | United Kingdom | 106/197 |
| 1221633 | 2/1971 | United Kingdom | 424/151 |

*Primary Examiner*—Sam Silverberg
*Attorney, Agent, or Firm*—John S. Roberts, Jr.

[57] ABSTRACT

A process of pretreating a lower alkyl cellulose, such as ethyl cellulose, which is to be used in microencapsulation of sodium fluoride for dental purposes. This process comprises dispersing a predetermined quantity of lower alkyl cellulose in an aqueous mineral acid, such as HCl, and stirring and aqueous washing of the cellulose such that the pH of the product is adjusted to 6.0 or less. This product is later dissolved in a BTX (benzene, toluene, xylene) solvent such as toluene. Sodium fluoride is added and process steps such as baffle stirring and drying are utilized to produce microencapsulation of the sodium fluoride with the lower alkyl cellulose. The process produces an encapsulating material of optimum sodium content and gives release time in water of 2.3–7.0 hours for the sodium fluoride.

5 Claims, No Drawings

METHOD OF PRODUCING DELAYED RELEASE OF SODIUM FLUORIDE

The present invention relates generally to the production of a delayed release of sodium fluoride, a material important in the field of dentistry and specifically in the area of preventive medicine in caries. The encapsulation of sodium fluoride is a chronic problem due to its extremely polar and hydrophilic qualities.

PRIOR ART STATEMENT

U.S. Pat. Nos. 1,448,091 Seel and 1,599,508 Altwegg et al teach the acid treatment of ethyl cellulose.

U.S. Pat. No. 3,049,537 Klug et al teaches the neutralization of hydroxyalkyl cellulose ethers with acetic or nitric acid.

Specifically, this process relates to a pretreatment of the encapsulating material, which is a lower alkyl cellulose, the term lower alkyl being defined as $C_1$–$C_6$ in the etherifying group on the cellulose. A preferred material, of course, is ethyl cellulose (Ethocel, Dow Chemical). As generally manufactured, such a lower alkyl cellulose contains ONa groups and is the rough input material for the process.

In a particular illustration, in Step (a) input ethyl cellulose is dispersed in aqueous HCl to obtain a product wherein the pH is less than 6.0. The pH is measured in a benzene/alcohol system 10:90. In Step (b) the acidified product from (a) of ethyl cellulose is dissolved in a BTX (benzene, toluene, xylene) solvent, such as toluene; then sodium fluoride is added with baffle stirring and drying to produce microencapsulation of the sodium fluoride with the ethyl cellulose. A product is obtained which has a typical size of 40–60$\mu$m. The process produces an encapsulating material of optimum sodium content and gives release time in water of 2.3–7.0 hours for the sodium fluoride.

The advantage in release rate over known methods is substantial for the present process. For example, in a typical application of coacervation the process will produce microcapsules in the range 140/230 mesh ($\equiv$62-1.5$\mu$m) containing 29–33% sodium fluoride, half of which is released in water over 2.3–7.0 hours. It has been further noted that microcapsules made by the same process but starting with untreated ethyl cellulose (pH 7–8) had a half release time in water of 0.7–0.9 hours. Further, release from the untreated Ethocel microcapsules was less linear than microcapsules made from pretreated ethyl cellulose.

EXAMPLE

Dow Standard 100 Ethocel (ethyl cellulose) was stirred vigorously in distilled water (1 liter for every 80–100 grams) in which 1 N hydrochloric acid was added gradually until the pH of the water was approximately 1.0. The dispersion was stirred and filtered and the Ethocel was washed repeatedly, then dried at a low temperature ($<$60° C.) at 30 mm Hg for 1–1½ hours. The product was tested by dissolving 2 grams in 100 ml of a solution containing 90% ethanol (190 proof) and 10% benzene (w/w). A pH reading of 6.0 or less was satisfactory.

The treated Ethocel was dissolved in toluene to make a 2% w/w solution. The solution was stirred at 1000 rpm in a baffled beaker. Three grams of finely ground sodium fluoride (size 40–60$\mu$m) were dispersed in 300 grams of solution. 120 grams of poly(dimethylsiloxane) (Dow Corning 360, 20 centistokes viscosity) were added at a constant rate over a 20-minute period followed by 400 ml petroleum ether (b.p. 35°–65° C.) over a 4-minute period, then 1.2 liters over a one-minute period. Stirring was discontinued after five additional minutes. The supernate was decanted and the fluffy white precipitate was washed five times with 400 ml portions of petroleum ether. In order to alleviate sticking, the precipitate was not allowed to settle completely before each portion of petroleum ether was poured off. After the fifth washing, the precipitate was filtered, dried (1 hour, 30 mm Hg, 70° C.) and sifted. This process produced 1.4–1.8 grams of 140/230 mesh ($\equiv$62–105$\mu$m) microcapsules containing 29–33% sodium fluoride, half of which was released in water over 2.3–4.3 hours. If a slower release is desired, cyclohexane is mixed with the petroleum ether used in the washing; for instance, when the third wash consisted of 40 ml cyclohexane and 150 ml petroleum ether, a similar yield of microcapsules which released half of their sodium fluoride in 7 hours was obtained. Microcapsules made by the same process but starting with untreated Ethocel (pH 7–8) had a half release time in water of 0.7–0.9 hours; release from these microcapsules was observably less linear than release from microcapsules made with pretreated Ethocel. The size and release rate of the microcapsules produced in this run was typical of other batches.

I claim:

1. A process of pretreating a lower alkyl cellulose to increase the aqueous release time of a later encapsulated sodium fluoride which comprises
    (a) dispersing a predetermined quantity of lower alkyl cellulose in aqueous mineral acid, stirring, aqueous washing, and filtering to adjust the pH to about 6.0 or less and to obtain a product;
    (b) dissolving the product of (a) in a BTX solvent, adding sodium fluoride and baffle stirring and drying to produce microencapsulation of said sodium fluoride with the lower alkyl cellulose product wherein the aqueous release time of the sodium fluoride is about 2.3–7.0 hours and the mesh size of particles if 40–60$\mu$m.

2. The process according to claim 1 wherein the lower alkyl cellulose is ethyl cellulose.

3. The process according to claim 1 wherein the aqueous mineral acid is hydrochloric acid.

4. The process according to claim 1 wherein the BTX solvent is toluene.

5. The process according to claim 1 wherein the pH is less than 6.0 as measured in a benzene/alcohol system 10/90.

* * * * *